United States Patent [19]

Marder et al.

[11] Patent Number: 5,674,529
[45] Date of Patent: Oct. 7, 1997

[54] ALKALINIZING POTASSIUM SALT CONTROLLED RELEASE PREPARATIONS

[75] Inventors: Herman Marder, Princeton; Lawrence Kirschner, Flanders, both of N.J.; John J. Steinke, Doylestown, Pa.; Andrew D. Kurtz, Belle Meade, N.J.; Poul Bertelsen; Nils Gjerlov Hansen, both of Frederiksberg, Denmark; Thyge Borup Hjorth, Farum, Denmark

[73] Assignee: Church & Dwight Co., Inc., Princeton, N.J.

[21] Appl. No.: 472,693

[22] Filed: Jun. 6, 1995

[51] Int. Cl.$^6$ .............................. A61K 9/22; A61K 9/26
[52] U.S. Cl. .................. 424/468; 424/469; 424/494; 424/497; 424/498; 424/495
[58] Field of Search .................... 424/468, 470, 424/490, 494, 495, 497, 498, 469

[56] References Cited

U.S. PATENT DOCUMENTS

| | | | |
|---|---|---|---|
| 4,140,756 | 2/1979 | Gallian | 424/21 |
| 4,259,315 | 3/1981 | Lippmann et al. | 424/37 |
| 4,572,833 | 2/1986 | Pedersen et al. | 424/20 |
| 4,574,080 | 3/1986 | Roswall et al. | 424/20 |
| 4,666,703 | 5/1987 | Kopf | 424/470 |
| 4,713,248 | 12/1987 | Kjorn et al. | 424/468 |
| 4,716,041 | 12/1987 | Kjornaes et al. | 424/468 |
| 4,728,513 | 3/1988 | Ventouras | 424/461 |
| 4,822,619 | 4/1989 | Eichel et al. | 424/492 |
| 4,863,743 | 9/1989 | Hsiao et al. | 424/476 |
| 4,882,169 | 11/1989 | Ventouras | 424/493 |
| 5,035,898 | 7/1991 | Chang et al. | 424/474 |
| 5,171,583 | 12/1992 | Morris, Jr. et al. | 424/717 |
| 5,445,805 | 8/1995 | Zuccarello et al. | 424/422 |
| 5,498,428 | 3/1996 | Morris, Jr. et al. | 424/717 |

FOREIGN PATENT DOCUMENTS

WO 90/04403  3/1990  WIPO.

*Primary Examiner*—Thurman K. Page
*Assistant Examiner*—James M. Spear
*Attorney, Agent, or Firm*—Bryan Cave LLP

[57] ABSTRACT

Multiparticulate controlled release preparations incorporating an alkalinizing potassium salt, preferably potassium bicarbonate, as an active ingredient, which are suitable for forming pharmaceutical dosage forms for oral administration. Such dosage forms are useful for potassium supplementation and for the treatment of degenerative bone or cardiovascular diseases, e.g., osteoporosis and hypertension.

11 Claims, 3 Drawing Sheets

ALKALINIZING POTASSIUM SALT CONTROLLED RELEASE PREPARATIONS

FIELD OF THE INVENTION

The present invention relates to multiparticulate controlled release preparations incorporating an alkalinizing salt of potassium as an active ingredient, which are suitable for forming pharmaceutical dosage forms for oral administration. Such dosage forms are useful for potassium supplementation and for the treatment of certain chronic diseases of aging, such as degenerative bone diseases, e.g., osteoporosis, or cardiovascular diseases, e.g., hypertension.

BACKGROUND OF THE INVENTION

It has been proposed to use alkalinizing potassium salts as active ingredients in the treatment of osteoporosis or hypertension. See Morris et al U.S. Pat. No. 5,171,583 granted Dec. 15, 1992, U.S. patent application Ser. No. 08/186,257 filed Jan. 10, 1994, now U.S. Pat. No. 5,498,428 granted Mar. 12, 1996, and PCT Published Application No. PCT/US89/04771. Such salts include potassium bicarbonate and other alkalinizing potassium salts which metabolize to the bicarbonate in vivo or otherwise produce the bicarbonate in vivo, e.g. potassium citrate ($K_3C_6H_5O_7 \cdot H_2O$) and potassium gluconate ($KC_6H_{11}O_7$). The alkalinizing potassium salt-containing dosage forms of the present invention are particularly suitable for oral administration in treatments for the foregoing indications. It has previously been proposed to orally administer various potassium salts, e.g., potassium chloride, for the treatment of hypokalemia. Potassium salts are, however, known to have a bitter taste and to be irritating to the gastrointestinal mucosa. Such salts must be coated with a controlled release coating both to mask their taste and to facilitate their sustained release in the gastrointestinal tract over an extended time period. A variety of potassium salt-containing oral dosage forms are known, including both liquids and encapsulated or tabletted, film-coated dosage forms incorporating wax matrix cores, multiparticulate cores or the like.

Liquid dosage forms of potassium salts are less palatable, inconvenient to use, and are, in general, not preferred when solid forms are available. For treatment of long term chronic conditions in particular, liquid formulations pose a number of difficulties. The potassium salts tend to be released from liquid formulation in large quantities, i.e. as a bolus. In addition, patient compliance is quite low due to the large quantity of liquids involved, and the bitter taste associated with release of the potassium salt.

Encapsulated multiparticulate dosage gelatin capsules are described in Lippman, et al., U.S. Pat. No. 4,259,315. Such gelatin capsule dosage forms are difficult to load with high dosages of alkalinizing potassium salts.

Wax matrix-core solid dosage forms, e.g., those described in Gallian, U.S. Pat. No. 4,140,756 have been disadvantageous because of their inability to provide wide dispersion of controlled release dosages in the gastrointestinal tract. For example, wax matrix solid dosage forms can leave agglomerates of waxy potassium salt crystals on the intestinal mucosa, posing the risk of possible ulceration.

The use of multiparticulate solid preparations has been specifically proposed for the oral administration of potassium chloride. Dosage forms incorporating such preparations provide for greater dispersion of the potassium chloride throughout the gastrointestinal tract after administration, thus decreasing the risk of localized irritation or ulceration. An example of such a multiparticulate dosage form is found in Eichel et al U.S. Pat. No. 4,822,619, which discloses the preparation of a micronized gastrointestinal irritant, such as potassium chloride, in a protective balm comprising a wax. Such mixture may be formed into microcapsules and used as the core for larger microcapsules or may, alternatively, be tabletted or encapsulated.

Additional examples of multiparticulate preparations of coated potassium chloride crystals have been described in the patent literature. For example, coating with water-insoluble film-forming materials alone or in combination with other water-insoluble or water-soluble film-forming materials to both retard release of the drug by decreasing dissolution rates and protect the gastrointestinal tract have been described in Lippmann et al. U.S. Pat. No. 4,259,315; Kopf U.S. Pat. No. 4,666,703; Kjornaes U.S. Pat. Nos. 4,713,248 and 4,716,041; Ventouras U.S. Pat. Nos. 4,728,513 and 4,882,169; Hsiao U.S. Pat. No. 4,863,743; and Chang et al. U.S. Pat. No. 5,035,898.

The coating of potassium chloride crystals with film-forming materials and immiscible hydrophobic waxes, e.g., paraffin wax, in order to both retard release of the drug and protect the gastrointestinal tract has also been described in the patent literature. See Pedersen et al. U.S. Pat. No. 4,572,833 and Roswall et al. U.S. Pat. No. 4,574,080.

It has been found that the effective oral dosage of an alkalinizing potassium salt in the treatment of degenerative bone or cardiovascular diseases such as osteoporosis or hypertension is about 15–200 milliequivalents (MEQ), preferably about 45–180 MEQ, per 70 kg patient weight per day. The use of potassium bicarbonate for such purposes is preferred since it permits the production of relatively high density (and, consequently, relatively low volume) dosage forms. In a particularly preferred embodiment, potassium bicarbonate may be administered at a dose of 60 MEQ (6 grams) per day. When, for example, potassium bicarbonate is thus administered in the form of four tablets daily, each such preferred oral dosage form should incorporate 1.5 grams of the potassium bicarbonate.

For ease of swallowing and good patient compliance, solid dosages of drugs intended for chronic administration to humans should preferably have a volume of not more than about 1 c.c. Larger size tablets are perceived as hard to swallow. To provide tablet dosage forms incorporating about 1.5 grams of potassium bicarbonate in a total volume of about 1 c.c., it is necessary to utilize potassium bicarbonate crystals having markedly greater particle sizes and markedly decreased specific surface areas as compared with currently available potassium bicarbonate crystalline products. Such crystals, and procedures for preparing the same, are described in U.S. patent application Ser. No. 08/058,579, filed May 6, 1993, now U.S. Pat. No. 5,445,805 granted Aug. 29, 1995, the disclosure of which is incorporated herein by reference.

It is also important, in providing such orally administrable alkalinizing potassium salt-containing dosage forms, to utilize extremely thin controlled release coatings, e.g., coatings comprising less than about 10% by weight of the dosage form, consistent with the foregoing volume limitations for patient compliance. Such coatings must mask the bitter taste of the alkalinizing salt yet provide for its controlled release to mimic the slow rate of release as it occurs naturally in foods (and thus avoid gastrointestinal irritation), and have sufficient strength and durability to sustain the compacting forces applied during conventional tabletting operations.

It is, accordingly, a principal object of the present invention to provide solid alkalinizing potassium salt-containing controlled release preparations, and orally administrable dosage forms incorporating the same, which meet the foregoing criteria.

SUMMARY OF THE INVENTION

The present invention relates to multiparticulate controlled release, orally administrable preparations incorporating an alkalinizing salt of potassium as an active ingredient, and solid dosage forms thereof. More specifically, the invention relates to preparations incorporating a multiplicity of single crystals of an alkalinizing potassium salt, the crystals having particle aspect ratios less than about 3:1, particle sizes greater than about 500μ, a weight mean particle size greater than about 700μ, and a B.E.T. surface area less than about 0.015 m²/gram; a coherent coating on each of the crystals, comprising a film-forming material which is insoluble in an aqueous environment, and a hydrophobic wax, the hydrophobic wax and the film-forming material being soluble in the same solvent, being compatible (miscible) with one another in solution, and forming a strong yet thin, permeable membrane in the dried coating; and the coated crystals being capable of being tabletted in a dosage form wherein the alkalinizing potassium salt is at least 75% by weight thereof.

It has been found that, by forming the crystal coating from a compatible film-forming material and hydrophobic wax, a strong yet thin permeable membrane is provided which masks the taste of the alkalinizing salt, provides precise, controlled release of the salt through the membrane (thus protecting the gastrointestinal mucosa against irritation), and permits the use of a thinner coating (and, hence, a greater density of active ingredient and, potentially, smaller volume tabletted dosage form) than heretofore possible.

In one particularly significant aspect of the controlled release preparation of the invention, it has been found that the permeable membrane thereof is sufficiently strong and flexible that, even after compacting for tabletting with minimum amounts of excipient, it substantially retains its original release characteristics. Thus, it has been shown that the % dissolution of the alkalinizing potassium salt from tabletted, dosage forms incorporating the coated crystals hereof is not appreciably greater than the % dissolution of the salt from the coated crystals prior to compacting and tabletting (the ratios of the release rates from the tabletted coated crystal forms to the release rates from the coated crystals themselves approaching unity—see Tables 2,4 and 6, and FIGS. 1A and 1B). On the other hand, coated crystals prepared from immiscible hydrophobic waxes of the prior art have been shown to have release rates after tabletting approaching ten fold those of the coated crystals prior to tabletting (see FIGS. 2A, 2B and 2C). These variations illustrate the markedly improved strength and controlled release characteristics of the preparations of the present invention.

By providing such a coating on the multiparticulate alkalinizing potassium salt crystals, and compounding them with an appropriate excipient, as described more fully hereinafter, it has been found possible to provide orally administrable dosage forms which exhibit characteristics substantially exceeding standard pharmaceutical requirements, e.g., have a friability less than 2%, frequently as low as 0.1–1%; a disintegration time less than 30 minutes, frequently as low as 5–15 minutes; and a % dissolution of less than 65%, frequently 25–50%, after two hours. Such dosage forms are quite suitable for the chronic administration of alkalinizing potassium salts in the treatment of, for example, osteoporosis and hypertension, are not irritating to the gastrointestinal mucosa, and are quite acceptable in regard to patient compliance (both as to taste and volume of the unit dosage form).

DETAILED DESCRIPTION OF THE INVENTION

Figure 1A:
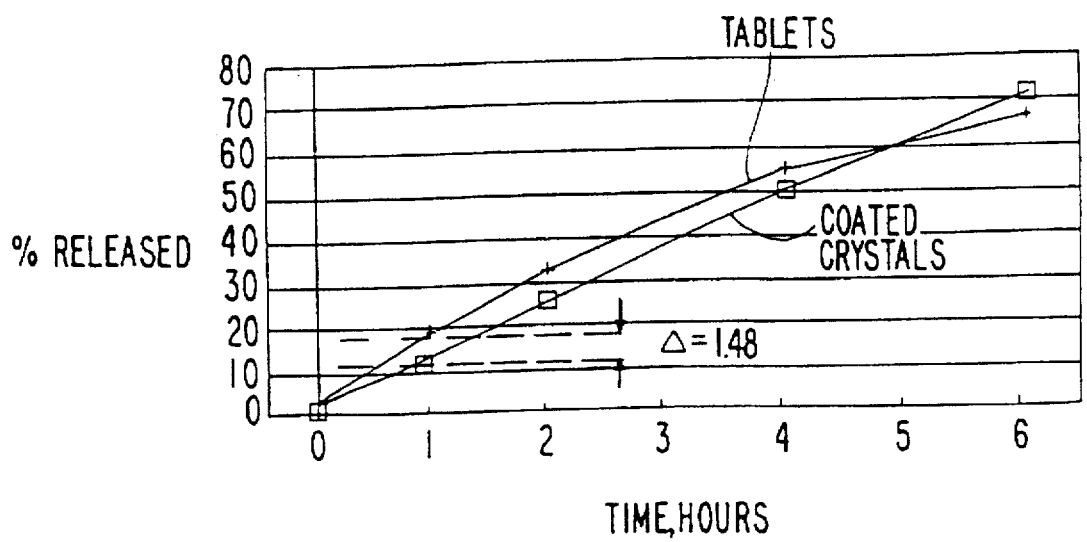
FIG. 1A and FIG. 1B are graphs showing the release characteristics (% dissolution) of potassium bicarbonate crystals coated with a compatible film-forming material and hydrophobic wax in accordance with Examples 10 and 11, indicating the ratio A of the degree of dissolution of the salt in the entabletted dosage forms as compared with the degree of dissolution from the coated crystals prior to tabletting.
Figure 1B:
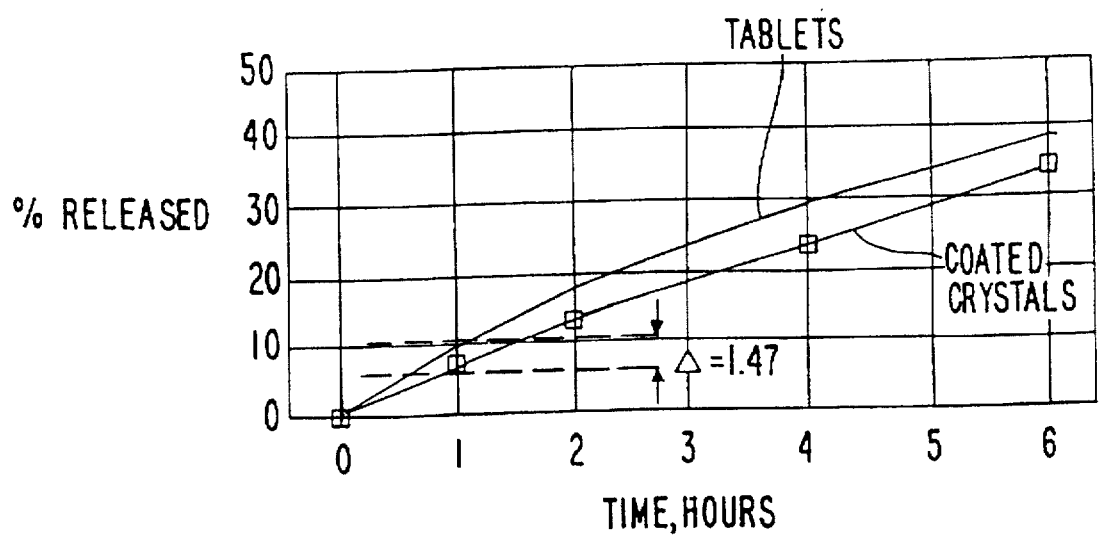

Alkalinizing salts of potassium are potassium salts which, upon oral administration, produce a slight systemic alkalinization in vivo. Upon ingestion of such alkalinizing potassium salts, they are metabolized or otherwise converted to bicarbonate. The alkalinizing potassium salts which may be utilized in the dosage forms of this invention are non-toxic at the dosages administered and are preferably selected from the group consisting of potassium bicarbonate and the non-toxic potassium salts of carboxylic acids, e.g., potassium citrate and potassium gluconate.

The use of potassium bicarbonate is particularly preferred in the dosage forms of the present invention, and is illustrated in the following description of preferred embodiments thereof. The bicarbonate is preferred because it is the form in which alkalinizing potassium salts frequently occur in foods, it is the form to which other alkalinizing salts are converted in vivo and, not insignificantly, because of its lower formula weight, a given number of milliequivalents of potassium bicarbonate requires a lesser volume than other alkalinizing potassium salts. However, it should be understood that other non-toxic, alkalinizing potassium salts may be incorporated in the multiparticulate controlled release preparations and pharmaceutical dosage forms hereof in accordance with the invention.

The preparation, isolation and purification of alkalinizing potassium salts are well-known to those skilled in the art, as such salts are commonly employed in a therapeutic setting for a variety of uses other than described herein. Specific protocols for preparing such salts are generally described in Remington's Pharmaceutical Sciences, Mack Publishing Company, Eastern, Pa., 16th Ed., 1982, which is incorporated herein by reference. Depending on the intended purpose, the multiparticulate controlled release preparations and orally administrable pharmaceutical dosage forms of the invention may be in the form of, for example, tablets, capsules, powders, granules, or the like, preferably in tablets suitable for administration of precise dosages. If desired, the oral dosage forms may also include other pharmaceutical agents.

The alkalinizing potassium salt crystals of the multiparticulate controlled release preparation comprise single crystals having aspect ratios less than about 3:1. As used herein, the aspect ratio refers to the ratio of the longest dimension of the crystal to the shortest dimension of the crystal. The crystals are shaped like regular solids having substantial sizes in all three dimensions, as distinguished from distinctly needle-, fiber-, or platelet-like shapes. Preferred crystals are unagglomerated, cubic crystals having relatively smooth surfaces. Such unagglomerated, cubic crystals pack well and leave relatively minute interstitial voids therebetween when subsequently coated with controlled release coatings, or blended and compacted with pharmaceutically acceptable excipients into tablets in accordance with the invention.

When utilizing potassium bicarbonate crystals to be compacted into a tablet dosage form, the crystals have a weight mean particle size greater than about 500µ, preferably within the range of about 800–900µ; and a specific B.E.T. surface area less than about 0.015 $m^2$/gram, preferably about 0.002–0.010 $m^2$/gram, and most desirably, about 0.004–0.010 $m^2$/gram. Desirably, the crystals have particle distributions such that over about 90 weight percent of the crystals have mean particle sizes within the range of about 700–1000µ and consequently, a dose density of at least about 13.0 milliequivalents per c.c.

The number of individual potassium bicarbonate crystals incorporated in the preferred tablet dosage form is not critical and will, of course, depend upon their individual particle sizes and the desired unit dosage. Generally, about 100–5,000 particles may be incorporated in a unit dosage containing 1.5 grams (15 milliequivalents) of potassium bicarbonate. Such unit dosage is acceptable when the potassium bicarbonate is administered at a total dosage of 60 MEQ (6 grams) per day, in four tablets. When the number of tablets administered per day or the desired dosage is modified, the number of potassium bicarbonate crystals in the unit dosage may, of course, be varied.

In accordance with the invention, each of the alkalinizing potassium salt crystals is coated with a water permeable, dried membrane coating comprising a film-forming material which is insoluble in an aqueous environment and a hydrophobic wax which are compatible with one another, i.e., they are soluble in the same solvent and miscible in the solution utilized to deposit the membrane coating. The compatibility of the film-forming material and the hydrophobic wax in the coating provides strong, coherent permeable membranes on the crystals. The permeable membranes provide a thin, strong coating capable of providing controlled release of the crystals in aqueous media.

Such coatings limit the dissolution rate of the alkalinizing potassium salt crystals by extending the length of time it takes for the salt to dissolve and permeate through the membrane. In addition, when tabletted, the thin, coherent, permeable coatings permit compression of the coated crystals upon blending with the excipient into a high density dosage form, the compatible components acting as protectants for the crystal coatings and insuring similar release characteristics in both the coated crystals and compacted tablets incorporating the same.

The hydrophobic wax incorporated in the crystal coatings acts in concert with the film-forming material to retard the diffusion of the alkalinizing potassium salt and protect the integrity of the coatings upon compaction of the crystals with excipient. The hydrophobic wax may be any pharmaceutically acceptable hydrophobic, waxy material which is capable of forming a continuous phase when dissolved with the film-forming material in an appropriate solvent, including synthetic waxes such as hydrogenated oils, e.g., hydrogenated castor oil and hydrogenated vegetable oil. The hydrophobic waxes useful in the formulations of the invention generally have melting temperatures of about 50°–125° C.

The film-forming materials incorporated in the crystal coatings are substantially water-insoluble, but permit water diffusion therethrough when dried. Such film-forming materials form continuous and water-permeable coatings when used alone or when admixed with the hydrophobic waxes in the crystal coatings. Examples of suitable film-forming substances are cellulose ethers, such as ethylcellulose, cellulose acetate phthalate; and acrylic acid-based polymers, e.g., water-insoluble ammonio-methacrylate copolymers. On the other hand, substantially water-soluble cellulose ethers such as hydroxypropylcellulose, carboxymethylcellulose, methylcellulose, propylcellulose, hydroxyethylcellulose, carboxyethylcellulose, carboxymethylhydroxyethylcellulose, hydroxymethylcellulose, carboxymethylethylcellulose, methylhydroxypropylcellulose or hydroxypropylmethylcellulose, are not suitable by themselves for use in the formulations of this invention, except as modifiers.

A particularly preferred crystal coating useful herein comprises hydrogenated castor oil as the hydrophobic wax and ethylcellulose as the water-insoluble film-forming material. The hydrogenated castor oil and ethylcellulose are highly compatible with one another and form permeable coatings when dried.

The alkalinizing potassium salt crystal coatings may be applied in single or multiple layers. When a single layer coating is utilized, it may comprise a mixture of the hydrophobic wax and the film-forming material. When a multiple layer coating is used, the layers may individually contain the hydrophobic wax, the film-forming material, or a mixture of the hydrophobic wax and the film-forming material. Those layers that contain the film-forming material may also include a plasticizer, e.g., acetyl tributyl citrate, triethyl citrate, diethyl phthalate, dibutyl phthalate, glycerol triacetate, dibutyl sebacate, or the like.

A preferred controlled release preparation of the present invention incorporates single layer crystal coatings comprising a mixture of the hydrophobic wax, the film-forming material and the plasticizer. Such mixtures provide the aforementioned permeable coatings when dried.

Preferred controlled release preparations of the invention incorporating dual layer coatings include a first, inner layer comprising the film-forming material and a plasticizer, or the hydrophobic wax; and a second, outer layer comprising a mixture of the hydrophobic wax, the film-forming material and the plasticizer. The first, inner layer provides greater protection of the crystals and decreased % dissolution over time, whereas the outer layer both controls the % dissolution rate and protects the coated crystals when subjected to compression during tabletting. It is particularly preferred to incorporate the film-forming material and the plasticizer in the first, inner layer to provide increased binding of the coating to the alkalinizing potassium salt substrate.

Preferred controlled release preparations of the present invention incorporating triple layer coatings include a first, inner layer comprising the film-forming material and the plasticizer; a second, intermediate layer comprising the hydrophobic wax; and a third outer layer comprising a mixture of the hydrophobic wax, the film-forming material and the plasticizer. Use of the film-forming material and the plasticizer in the first, inner layer and the mixture of the hydrophobic wax, the film-forming material and the plasticizer in the third, outer layer are preferred. Use of the hydrophobic wax in the second, intermediate layer provides for a decreased dissolution rate through the substantially homogeneous hydrophobic layer, increased protection to the gastrointestinal tract, and improved glidant and protectant function of the coatings when the coated crystals are compacted into a tablet dosage form.

In forming the coatings, the several ingredients are initially dissolved in an organic solvent to form an appropriate coating lacquer. Examples of suitable solvents are alcohols, e.g. isopropanol, ethanol and methanol; toluene and toluene-alcohol mixtures; ketones, e.g. acetone; and chlorinated hydrocarbons, e.g., methylene chloride.

The coated crystals may be prepared by any conventional coating operation, desirably by a fluidized bed co-current coating technique. When so applied, the coating lacquer components are initially mixed at temperatures sufficient to fully dissolve the individual ingredients in the solvent. When the ingredients are thoroughly dissolved, the mixture is clear to translucent. The coating lacquer is held at a temperature suitable for maintaining the lacquer components in a dissolved state, and is thereafter sprayed into the fluidized bed containing the fluidized alkalinizing potassium salt crystals. The crystals undergo multiple coating cycles for about 1–3 hours. The product temperature is maintained at less than about 60° C. throughout the process. Solvent is flash-evaporated from the crystals in the fluidized bed, leaving a continuous, permeable membrane in the dried coating. Preferably, an anhydrous solvent should be utilized in the coating operation and the fluidization technique should be carried out in dehumidified, very dry process air.

In a preferred embodiment of the invention, the coated crystals are blended and compacted with a pharmaceutically acceptable excipient to provide a tablet dosage form wherein the alkalinizing potassium salt is present in a dose density of at least about 11.18, preferably about 13.0–17.0, MEQ per c.c. The alkalinizing potassium salts are incorporated in such a dosage form in an amount of at least about 75% by weight, and preferably about 80–90% by weight, of the total tablet weight.

For preparation of the tablet dosage forms, the coated alkalinizing potassium salt crystals are blended and compacted with pharmaceutically acceptable excipients that may include conventional lubricants, disintegrants and binders. The excipient and coated crystals are suitably blended using a mixer, and tabletted in a single punch tablet press. Examples of suitable lubricants which may be incorporated in the excipients in the dosage forms of this invention include hydrophobic waxes, e.g., hydrogenated castor oil and hydrogenated vegetable oil, salts of stearyl fumarate, talc, and stearic acid and its salts. Examples of suitable disintegrants which may be incorporated in the excipients include natural starch, pregelatinized starch, sodium bicarbonate, cross-linked polyvinylpyrrolidone and cross-linked carboxymethyl cellulose sodium NF (croscarmellose sodium). Examples of suitable binders which may be incorporated in the excipients include colloidal silica, microcrystalline cellulose, ethylcellulose or other cellulose ethers, gelatin, glucose, acacia, polyvinylpyrrolidone, and starch.

Particularly preferred tablet dosage forms of the present invention which incorporate single layer coated crystals, incorporate crystal coatings comprising mixtures of the hydrophobic wax in an amount of about 0.25–3.0 weight % of the dosage form, the film-forming material in an amount of about 1–8 weight % of the dosage form, and a plasticizer in an amount of about 0–1 weight % of the dosage form.

Particularly preferred tablet dosage forms which incorporate double layer crystal coatings incorporate coatings comprising a first, inner layer containing the film-forming material, in an amount of about 1–5 weight % of the dosage form, and a plasticizer in an amount of about 0–1 weight % of the dosage form, or the hydrophobic wax in an amount of about 0.1–2.0 weight % of the dosage form; and a second, outer layer primarily comprising the film-forming material, in an amount of about 1–5 weight % of the dosage form, the plasticizer in an amount of about 0–1 weight % of the dosage form, and the hydrophobic wax in an amount of about 0.1–2.0 weight % of the dosage form.

Particularly preferred tablet dosage forms incorporating triple layer coatings comprise a first, inner layer primarily comprising the film-forming material, in an amount of about 1–5 weight % of the dosage form and a plasticizer in an amount of about 0–1 weight % of the dosage form; a second, intermediate layer primarily comprising the hydrophobic wax, in an amount of about 0.1–2.0 weight % of the dosage form; and a third, outer layer primarily comprising the film-forming material, in an amount of about 1–5 weight % of the dosage form, the plasticizer in an amount of about 0–1 weight % of the dosage form, and the hydrophobic wax in an amount of about 0.1–2.0 weight % of the dosage form.

Particularly preferred excipients useful in producing the tablet dosage forms contain a hydrophobic wax which may be the same as or is compatible with the hydrophobic wax in the crystal coating, e.g., hydrogenated castor oil alone or admixed with hydrogenated vegetable oil, in an amount of about 0.30–3.0 weight % of the dosage form; a disintegrant, e.g., cornstarch, in an amount of about 0–10 weight % of the dosage form; and a binder, e.g., a mixture of microcrystalline cellulose and colloidal silica, in an amount of about 1–10 weight % of the unit dosage.

Preferred specific embodiments of the dosage forms of this invention are described in the following examples. As used in the examples and elsewhere in this specification, the % friability of a given tablet dosage form is a measure of the fragility of the tablet. The lower the friability, the greater the ability of such a tablet dosage form to resist breakage upon handling. Friability is determined in accordance with Pharmacopoeial Forum, (12/16), March–April 1990, page 299. Dust is removed from a sample of tablets which are weighed and subjected to rotation. Dust is removed from the tablets as before and weighed. The loss of weight is calculated as a percentage of the initial weight. This percentage or friability is defined as the weight loss in % w/w. For specific testing procedures see footnote 4 to Table 2.

As further used herein, the disintegration time refers to the time for a given tablet dosage form to completely break apart in a controlled testing apparatus, and is a measure of the time elapsed between introduction of a tablet into water and the passage of materials through a sieve. Disintegration times are calculated according to the European Pharmacopoeia, Second Edition, V.5.11. For specific testing procedures see footnote 5 to Table 2. Disintegration time analysis is not carried out beyond 30 minutes.

Finally, as further utilized in the examples and otherwise in this specification, the % dissolution of a given tablet dosage form is a function of the dissolution of the alkalinizing potassium salt, e.g., potassium bicarbonate, in a controlled test. The % dissolution is determined according to the U.S. Pharmacopoeia XXII, p. 1579 (Para. 711), 1990, using the basket method (Method I) at 100 rpm. The dissolution rate is affected both by the coating on the crystals and the components of the excipients.

EXAMPLES 1-3 AND COMPARATIVE EXAMPLES A AND B

Dosage Forms Incorporating Single Layer Coatings on Potassium Bicarbonate Crystals Examples 1-3 below describe the preparation of dosage forms within the scope of the present invention incorporating multiparticulate potassium bicarbonate crystals coated with single layer coatings comprising ethylcellulose as the film-forming material thereof and hydrogenated castor oil as the hydrophobic wax constituent thereof.

A. Preparation of the Potassium Bicarbonate Crystals

Potassium bicarbonate crystals were prepared as described in the aforesaid U.S. patent application Ser. No. 08/058,579, now U.S. Pat. No. 5,445,805. The crystals used had a mean particle size within the range of 800–900µ, a B.E.T. surface area of 0.004–0.01 $m^2$/gram and particle distributions such that over 90% by weight of the crystals were within the range of 700–1000µ. (At least 90% of the crystals were retained on a 25 mesh screen [707µ] and less than 10% were retained on an 18 mesh screen [1000µ].) 3000 g of potassium bicarbonate crystals were used in each batch to be coated.

B. Preparation and Application of Controlled Release Coating Lacquers

Hydrogenated castor oil (CUTINA HR®, Henkel, U.S.), ethylcellulose (ETHOCEL® Standard 100 premium, Dow Chemical Co., U.S.) and acetyl tributyl citrate (Croeda Universal, Ltd., England) were dissolved in isopropyl alcohol to provide the controlled release coating lacquers. The CUTINA HR®, ETHOCEL® and acetyl tributyl citrate were dissolved in the isopropyl alcohol solvent by heating in a mixer equipped with a heating jacket set at 60°–70° with vigorous agitation. The agitation was continued for about one hour. When dissolved, the mixture was clear to translucent. The coating lacquer composition was maintained at temperatures of 60°–70° C.

The lacquers were coated on the potassium bicarbonate particles by co-current flow through a fluidized bed in which the moisture content was controlled. The coating lacquer was sprayed from a spray nozzle positioned at the bottom of a GLATT GPCG 3 (GLATT GmbH, Germany) fluidized bed apparatus equipped with a Wurster tube. The potassium bicarbonate crystals were fluidized and the warm coating lacquer was sprayed on the crystals in multiple coating cycles. The process air flow rate was adjusted as necessary to provide adequate movement of the crystals through the fluidized bed as they were coated.

During the coating process, the isopropyl alcohol solvent was flash-evaporated from the crystals as they cycled through the fluidized bed. After completing the application of the coating lacquer to the crystals, any trace residual solvent remaining on the coated crystals was removed by cycling in the fluidized bed without lacquer spray for 10 minutes. Following the residual solvent removal, the coated crystals were cooled in the bed. The amount of coating lacquer applied on the crystals was calculated as the % w/w of the dry matter of the respective coatings, relative to the uncoated potassium bicarbonate crystals. The compositions of the coating lacquers utilized in Examples 1-3 and Comparative Examples A and B, the coating conditions used in the respective examples, and the theoretical, total and percent yields of the coated crystals, as well as the calculated % w/w of the coatings are summarized in Table 1:

TABLE 1

Compositions and Conditions Used in Formation of Single Layer Coated Crystals

| | Example 1 | Example 2 | Example 3 | Comp. Ex. A | Comp. Ex. B |
|---|---|---|---|---|---|
| Coating Lacquer Composition: | | | | | |
| CUTINA HR ® (grams) | 23.45 | 19.25 | 15.40 | 14.85 | 18.76 |
| ETHOCEL ® (grams) | 163.45 | 163.45 | 130.76 | 126.09 | 130.76 |
| Acetyl Tributyl Citrate | 8.75 | 8.75 | 7.00 | 6.75 | 7.00 |
| Isopropyl Alcohol (grams) | 3304.35 | 3308.55 | 2646.84 | 2552.31 | 2643.48 |
| Total (grams) | 3500.00 | 3500.00 | 2800.00 | 2700.00 | 2800.00 |
| Coating Conditions: | | | | | |
| Process Air Flow ($m^3$/hr) | 100–171 | 100–180 | 99–166 | 115–127 | 50–160 |
| Spray Period (mins.) | 135 | 145 | 100 | 102 | 114 |
| Spray Temperature (°C.) | 60.1–68.1° | 61.5–68.1° | 63.0–63.9° | 62.7–65.3° | 63.0–67.6° |
| Spray Pressure (bars) | 2.0 | 2.0 | 2.0 | 2.0 | 2.0 |
| Liquid Flow Rate (g/min.) | 26–28 | 26–27 | 28–29 | 26 | 26–27 |
| Product Temperature (°C.) | 46–52° | 42–45° | 46–50° | 45–52° | 45–47° |
| Coated Crystals: | | | | | |
| Theoretical Yield (gms) | 3191.1 | 3186.9 | 3151.2 | 3134.0 | 3154.5 |
| Actual Yield (gms) | 3141.7 | 3122.0 | 3097.0 | 3087.6 | 3078.0 |
| % Yield | 98.5% | 98.0% | 98.8% | 98.5% | 97.6% |
| % of W/W Dry Matter (coating/uncoated crystals) | 6.37% | 6.23% | 5.04% | 4.45% | 5.15% |

C. Preparation of Multiparticulate Tablets

The excipients for the respective dosage forms comprised a hydrophobic wax as a lubricant (CUTINA HR®), mixtures of microcrystalline cellulose (AVICEL® PH 102) and colloidal silica (SYLOID®—W. R. Grace & Co., U.S.) as a binder, cornstarch as a disintegrant and hydrogenated vegetable oil (LUBRITAB®, Mendell, U.S.) as a punch lubricant. The multi-particulate coated crystals were mixed with the excipients in an Erweka AR 400 cubic mixer (J. Engelsman AG, Germany), in the following proportions:

| Constituents | Grams of Constituent Added to Mixer | % dry weight of dosage form |
|---|---|---|
| Potassium Bicarbonate Coated Crystals | 850.00 | 85.00 |
| CUTINA HR ® | 15.00 | 1.50 |
| AVICEL ® PH | 76.80 | 7.68 |
| Cornstarch | 51.20 | 5.12 |
| SYLOID ® | 4.00 | 0.40 |
| LUBRITAB ® | 3.00 | 0.30 |
| Total | 1000.00 | 100. |

The resulting mixture was then tabletted in a Fette Hanseaten Exacta I single punch tablet press (Fette, Germany), equipped with a means for monitoring the applied force on the upper and lower punches, respectively. Each tablet thus produced contained 1500 mg potassium bicarbonate.

The compositions of the excipients and the composite tablets, the weights, volumes, hardness and friability properties of the tablets, and the disintegration and dissolution characteristics of the respective tablets of Examples 1–3 and Comparative Examples A and B are given in Table 2:

strates the requirement for higher levels of ETHOCEL® where higher levels of CUTINA HR® are utilized in the coatings.

EXAMPLE 4 AND COMPARATIVE EXAMPLE C

Dosage Forms Incorporating Double Layer Coatings on Potassium Bicarbonate Crystals Example 4 describes the preparation of dosage forms incorporating multiparticulate potassium bicarbonate crystals coated with double layer coatings comprising ethylcellulose as the film-forming material thereof and hydrogenated castor oil as the hydrophobic wax constituent thereof.

A. Preparation and Application of Controlled Release Coating Lacquers

The same potassium bicarbonate crystals and coating materials were used as in the foregoing examples. The crystals were coated with two layers of coating lacquer. The first, inner layer coating lacquer comprised isopropyl alcohol and CUTINA HR®; the second, outer layer coating lacquer comprised a mixture of isopropyl alcohol, ETHOCEL®, acetyl tributyl citrate, and CUTINA HR®.

The composition of the coating lacquers utilized for each layer, the coating conditions used in the respective examples, and the theoretical, total and percent yields of the coated crystals, as well as the calculated % w/w of the coatings are summarized in Table 3.

Each coating lacquer mixture was prepared as in Example 1, and the crystals were coated with the lacquers according

TABLE 2

Compositions, Properties and Characteristics of Tablets Incorporating Single Layer Coated Crystals

| | Example 1 | Example 2 | Example 3 | Comp. Ex. A | Comp. Ex. B |
|---|---|---|---|---|---|
| Tablet Composition: | | | | | |
| CUTINA HR ® in coating (% W/W of dosage form) | 0.76% | 0.62% | 0.50% | 0.44% | 0.62% |
| CUTINA HR ® in excipient (% W/W of dosage form) | 1.50% | 1.50% | 1.50% | 1.50% | 1.50% |
| Total CUTINA HR ® (% W/W of dosage form) | 2.26% | 2.12% | 2.00% | 1.94% | 2.12% |
| ETHOCEL ® in coating (% W/W of dosage form) | 5.3% | 5.8% | 4.3% | 3.6% | 4.3% |
| Tablet Properties: | | | | | |
| Average Tablet Weight (grams)[1/] | 1.894 | 1.875 | 1.854 | 1.843 | 1.854 |
| Average Tablet Volume (c.c.)[2/] | — | 1.08 | 1.05 | 1.05 | — |
| Average Tablet Hardness (Newtons)[3/] | 108.5 | 115.5 | 111. | 102 | 134.5 |
| Tablet Characteristics: | | | | | |
| Friability (%)[4/] | 0.82% | 0.6% | 1.2% | 3.8% | 0.18% |
| Disintegration Time (minutes)[5/] | 3–23 | 4–6 | 3–6 | 2–6 | 9–30 |
| TAB/CC Ratio[6/] | 1.8 | 2.0 | 1.5 | 1.3 | 1.1 |
| % Dissolution (1 hr.)[7/] | 20.1% | 23.8% | 26.8% | 29.1% | 19.7% |
| % Dissolution (2 hr.)[7/] | 35.6% | 40.5% | 42.3% | 46.1% | 36.5% |
| % Dissolution (4 hr.)[7/] | 56.9% | 62.4% | 65.6% | 66.8% | 56.4% |
| % Dissolution (6 hr.)[7/] | 69.4% | 76.3% | 76.6% | 76.4% | 69.3% |

The tablets described in Comparative Example A contained 0.44% CUTINAHR® and 3.6% ETHOCEL® in the crystal coatings. Those tablets did not exhibit sufficient adhesion between the coated crystals to allow for a suitable tablet strength, i.e., less than 2% friability, upon tabletting.

The tablets described in Comparative Example B contained 2.12% CUTINA HR® and 4.3% ETHOCEL® in the crystal coatings. This quantity of ETHOCEL® was not adequate to offset the adhesive characteristics provided to the crystals by the CUTINA HR® and thus, the disintegration time of the tablets was increased. Example 2 demonto the methods described in Example 1. Following coating of the first layer, the second layer coating lacquer mixture was applied to the coated crystals in the fluidized bed.

TABLE 3

Compositions and Conditions Used in Formation of Double Layer Coated Crystals

|  | Example 4 and Comparative Example C | |
| --- | --- | --- |
|  | Layer 1 | Layer 2 |
| Coating Lacquer Composition: | | |
| CUTINA HR ® |  | 25.80 |
| ETHOCEL ® | 51.37 |  |
| Acetyl Tributyl Citrate | 2.75 |  |
| Isopropyl Alcohol | 1045.88 | 490.2 |
| Total | 1100.00 | 516.00 |
| Coating Conditions: | | |
| Process Air Flow (m³/hr) | 50–73 | 55–125 |
| Spray Period (mins.) | 17 | 66 |
| Spray Temperature (°C.) | 64.0–64.08° | 61.1–64.4° |
| Spray Pressure (bars) | 2.0 | 2.0 |
| Liquid Flow Rate (g/min.) | 26–28 | 26 |
| Product Temperature (°C.) | 42–51 | 41–45 |
| Coated Crystals: | | |
| Theoretical Yield (gms) | 3118.8 | |
| Actual Yield (gms) | 3049.0 | |
| % Yield | 97.8% | |
| % of W/W Dry Matter (coating/uncoated crystals) | 3.96 | |

B. Preparation of Multiparticulate Tablets

The excipient utilized in Example 4 was identical to that of Examples 1–3 and Comparative Examples A and B. The excipient utilized in Comparative Example C was similar, except that 7.5 grams of CUTINA HR® (0.75% CUTINA HR®), 81.3 grams of AVICEL® and 54.2 grams of cornstarch were used. In each case, the coated crystals and excipient were mixed and tabletted as in Example 1.

The compositions of the excipients and the composite tablets, the weights, volumes, hardness and friability properties of the tablets, and the disintegration and dissolution characteristics of the respective tablets of Example 4 and Comparative Example C are given in Table 4.

TABLE 4

Compositions, Properties and Characteristics of Tablets Incorporating Double Layer Coated Crystals

|  | Example 4 | Comp. Ex. C |
| --- | --- | --- |
| Tablet Composition: | | |
| CUTINA HR ® in coating (% W/W of dosage form) | 1.16% | 1.16% |
| CUTINA HR ® in excipient (% W/W of dosage form) | 1.50% | 0.75% |
| Total CUTINA HR ® (% W/W of dosage form) | 2.66% | 1.91% |
| ETHOCEL ® in coating (% W/W of dosage form) | 2.65% | 2.65% |
| Tablet Properties: | | |
| Average Tablet Weight (grams)[1/] | 1.834 | 1.834 |
| Average Tablet Volume (c.c.)[2/] | 1.04 | 1.04 |
| Average Tablet Hardness (Newtons)[3/] | 125 | 131 |
| Tablet Characteristics: | | |
| Friability (%)[4/] | 0.81% | 0.1% |
| Disintegration Time (minutes)[5/] | 7–11 | 3 |
| TAB/CC Ratio[6/] | 2.0 | 2.5 |
| % Dissolution (1 hr.)[7/] | 43.0% | 53.9% |
| % Dissolution (2 hr.)[7/] | 55.8% | 76.5% |
| % Dissolution (4 hr.)[7/] | 80.1% | 78.4% |
| % Dissolution (6 hr.)[7/] | 84.0% | 91.5% |

See Table 2 for footnotes 1–7.

The tablets described in Comparative Example C comprised the same coated crystals as Example 4. The difference was the decreased concentration of CUTINA HR® in the excipient of Comparative Example C (0.75%), as compared with Example 4 (1.50%). While the tablets of Example 4 exhibited marginal dissolution retardation, the decreased level of CUTINA HR® in the 0.75% excipient of Comparative Example C did not provide sufficient adhesion between the coated crystals or for sufficient protection of the crystal coating upon compaction and thus, the dissolution rate was increased.

An additional tablet dosage form coated with double layer coatings is prepared from a first, inner layer coating lacquer comprising isopropyl alcohol, ETHOCEL® and acetyl tributyl citrate; and a second, outer layer coating lacquer comprising a mixture of isopropyl alcohol, ETHOCEL®, acetyl tributyl citrate, and CUTINA HR®. The potassium bicarbonate crystals are coated with the lacquers, as described in the preceding examples, and blended and compacted with excipient, as described in the preceding examples. This embodiment comprises crystal coatings incorporating an ethylcellulose/acetyl tributyl citrate inner layer and an ethylcellulose/acetyl tributyl citrate/hydrogenated castor oil outer layer.

EXAMPLES 5–8 AND COMPARATIVE EXAMPLES D AND E

Dosage Forms Incorporating Triple Layer Coatings on Potassium Bicarbonate Crystals Examples 5–8 describe the preparation of dosage forms incorporating multiparticulate potassium bicarbonate crystals coated with triple layer coatings comprising ethylcellulose as the film-forming material thereof and hydrogenated castor oil as the hydrophobic wax constituent thereof.

A. Preparation and Application of Controlled Release Coating Lacquers

The same potassium bicarbonate crystals and coating materials were used as in the foregoing examples. The crystals were coated with three layers of coating lacquer. The first, inner layer coating lacquer comprised isopropyl alcohol, ETHOCEL® and acetyl tributyl citrate; the second, intermediate layer coating lacquer comprised isopropyl alcohol and CUTINA HR®; and the third, outer layer coating lacquer comprised a mixture of isopropyl alcohol, ETHOCEL®, acetyl tributyl citrate, and CUTINA HR®.

The composition of the coating lacquers utilized for each layer in Examples 5–8, the coating conditions used in the respective examples, and the theoretical, total and percent yields of the coated crystals, as well as the calculated % w/w of the coatings are summarized in Table 5.

Each coating lacquer mixture was prepared, and the crystals were coated with the lacquers, as described in the preceding examples. Each layer was sequentially applied utilizing the fluidized bed apparatus, as described above.

Excipients utilized for such tablet dosage forms were as described in the preceding examples. The mixtures of coated crystals and excipients are mixed and tabletted as in Example 1.

CUTINA HR®) and the excipient utilized in Comparative Example D was similar to those employed in the foregoing examples with the exception that no CUTINA HR® was added (0% CUTINA HR®), 85.8 grams AVICEL® and 57.2

TABLE 5

Compositions and Conditions Used in Formation of Triple Layer Coated Crystals

|  | Example 5 and 6 | | | Example 7 and Comp. Ex. D | | | Examples 8 and Comp. Ex. E | | |
| --- | --- | --- | --- | --- | --- | --- | --- | --- | --- |
|  | Layer 1 | Layer 2 | Layer 3 | Layer 1 | Layer 2 | Layer 3 | Layer 1 | Layer 2 | Layer 3 |
| Coating Lacquer Composition: | | | | | | | | | |
| CUTINA HR ® |  | 25.80 | 9.90 |  | 25.80 | 9.90 |  | 12.0 | 9.90 |
| ETHOCEL ® | 51.37 |  | 84.06 | 84.06 |  | 84.06 | 51.37 |  | 84.06 |
| Acetyl Tributyl Citrate | 2.75 |  | 4.50 | 4.50 |  | 4.50 | 2.75 |  | 4.50 |
| Isopropyl Alcohol | 1045.88 | 490.2 | 1701.54 | 1711.44 | 490.20 | 1701.54 | 1045.88 | 504.0 | 1701.54 |
| Total | 1100.0 | 516.00 | 1800.00 | 1800.00 | 516.00 | 1800.00 | 1100.00 | 516.0 | 1800.00 |
| Coating Conditions: | | | | | | | | | |
| Process Air Flow | 100–160 | 50–90 | 95–135 | 101–164 | 55–76 | 63–115 | 128–150 | 55–110 | 85–120 |
| Spray Period (mins.) | 31 | 14 | 57 | 65 | 15 | 55 | 28 | 15 | 62 |
| Spray Temperature (°C.) | 61.4–63.2° | 60.5–61.4° | 61.9–67.7° | 60.4–62.7° | 60.0–62.6° | 63.0–65.4° | 61.5–63.4° | 60.0–63.0° | 61.8–67.5° |
| Spray Pressure (bars) | 2.0 | 2.0 | 2.0 | 2.0 | 2.0 | 2.0 | 2.0 | 2.0 | 2.0 |
| Liquid Flow Rate (g/min.) | 27 | 25–28 | 26–28 | 27–30 | 24–26 | 26–27 | 26 | 25 | 26 |
| Product Temperature | 45–50° C. | 38–45° | 40–46° | 44–54° | 44° | 44–45° | 45–50° | 38–45° | 37–45° |
| Coated Crystals: | | | | | | | | | |
| Theoretical Yield (gms) | 3171.0 | | | 3202.5 | | | 3157.2 | | |
| Actual Yield (gms) | 3098.0 | | | 3137.6 | | | 3190.0 | | |
| % Yield | 97.7% | | | 98.0% | | | 98.5% | | |
| % of W/W Dry Matter (coating/uncoated crystals) | 5.70% | | | 6.75% | | | 5.24% | | |

B. Preparation of Multiparticulate Tablets

The excipients utilized in Examples 5 and 7 were identical to those employed in Examples 1–3 (1.50% CUTINA HR®). The excipients utilized in Examples 6 and 10 were identical to that employed in Example 4 (0.75% CUTINA HR®). The excipient utilized Comparative Example E was identical to those employed in Examples 1–3 (1.50% grams cornstarch were added. In each case, the mixtures of coated crystals and excipients were mixed and tabletted as in Example 1.

The compositions of the excipients and the composite tablets, the weights, volumes, hardness and friability properties of the tablets, and the disintegration and dissolution characteristics of the respective tablets of Examples 5–8 and Comparative Examples D and E are given in Table 6:

TABLE 6

Compositions, Properties and Characteristics of Tablets Incorporating Triple Layer Coated Crystals

|  | Example 5 | Example 6 | Example 7 | Comp. Ex. D | Example 8 | Comp. Ex. E |
| --- | --- | --- | --- | --- | --- | --- |
| Tablet Composition: | | | | | | |
| CUTINA HR ® in coating (% W/W of dosage form) | 1.16% | 1.16% | 1.13% | 1.13% | 0.70% | 0.70% |
| CUTINA HR ® in excipient (% W/W of dosage form) | 1.50% | 0.75% | 1.50% | 0% | 1.50% | 0.75% |
| Total CUTINA HR ® (% W/W of dosage form) | 2.66% | 1.95% | 2.63% | 1.13% | 2.20% | 1.45% |
| ETHOCEL ® in coating (% W/W of dosage form) | 4.3% | 4.3% | 6.3% | 6.3% | 4.3% | 4.3% |
| Tablet Properties: | | | | | | |
| Average Tablet Weight (grams)[1] | 1.866 | 1.866 | 1.860 | 1.837 | 1.856 | 1.856 |
| Average Tablet Volume (c.c.)[2] | 1.07 | 1.07 | 1.08 | 1.09 | 1.05 | 1.06 |
| Average Tablet Hardness (Newtons)[3] | 115 | 121 | 110.7 | 152 | 129 | 130 |

TABLE 6-continued

Compositions, Properties and Characteristics of Tablets Incorporating Triple Layer Coated Crystals

| | Example 5 | Example 6 | Example 7 | Comp. Ex. D | Example 8 | Comp. Ex. E |
|---|---|---|---|---|---|---|
| Tablet Characteristics: | | | | | | |
| Friability (%)[4] | 0.2% | 0.2% | 0.35% | 0.1% | 0.3% | 0.25 |
| Disintegration Time (minutes)[5] | 2–7 | 3–5 | 4–15 | 1–2+ | 5–13 | 2–7 |
| TAB/CC Ratio[6] | 2.0 | 2.5 | 1.6 | 5.9 | 1.1 | 3–4 |
| % Dissolution (1 hr.)[7] | 14.4% | 18.0% | 10.0% | 33.7% | 14.8% | 35.5% |
| % Dissolution (2 hr.)[7] | 22.7% | 28.2% | 17.6% | 48.8% | 26.0% | 52.5% |
| % Dissolution (4 hr.)[7] | 40.3% | 47.5% | 29.4% | 65.6% | 41.1% | 69.7% |
| % Dissolution (6 hr.)[7] | 43.1% | 56.6% | 38.7% | 73.3% | 54.5% | 82.7% |

See Table 2 for footnotes 1–7.

The tablets described in Comparative Examples D and E comprised the same coated crystals as in Example 7 and 8, respectively. The decreased levels of CUTINA HR® in the Comparative Examples did not provide sufficient protection during tabletting, resulting in substantial damage to the coated crystals as reflected in the relatively high TAB/CC ratios thereof.

EXAMPLES 9 AND 10, AND COMPARATIVE EXAMPLES F–H

Comparison of Dosage Forms Incorporating Different Film Formers/Hydrophobic Waxes The release characteristics of formulations incorporating a compatible film-forming material (ethylcellulose) and hydrophobic wax (hydrogenated castor oil), both of which were soluble in isopropanol (Examples 9 and 10) with formulations incorporating an incompatible film forming material (ethylcellulose) and hydrophobic wax (paraffin wax), i.e., which were not soluble in the same solvent (isopropanol) and miscible therein (Comparative Examples F–H) was compared.

The respective formulations differed primarily in that CUTINA HR® was incorporated in the coatings of Examples 9 and 10, whereas a paraffin wax, Hard Paraffin (as defined by the British Pharmacopoeia), was incorporated in the coatings of Comparative Examples F–H. Single layer coatings were provided on the preparations of each of Examples 10 and Comparative Examples F–H and were prepared in the manner described in Example 1. A triple layer coating was provided on the crystals of Example 10, prepared as described in Examples 5–8. (Comparative Examples F–H are analogous to Example 1 of both Pedersen, et al., U.S. Pat. No. 4,572,833 and Roswall, et al., U.S. Pat. No. 4,574,080.) In each case the excipient had the same composition, and was prepared in the same manner, as described in Example 1. The release characteristics of the respective coated crystal preparations and tabletted dosage forms are given in Table 7 below:

TABLE 7

Comparison of Release Characteristics of Potassium Bicarbonate from Formulations Incorporating Different Film Formers/Hydrophobic Waxes

| | % Dissolution[7] of Potassium Bicarbonate After: | | | | | | |
|---|---|---|---|---|---|---|---|
| Example | 1 Hr. | 2 Hrs. | 4 Hrs. | 6 Hrs. | 10 Hrs. | 15 Hrs. | TAB/CC[6] after 1 Hr. |
| Example 9 Tablet | 17.3 | 31.0 | 53.6 | 66.6 | 82.9 | — | 1.47 |
| Coated Crystal | 11.7 | 23.9 | 48.6 | 71.4 | 88.2 | — | |
| Example 10 Tablet | 10.0 | 17.6 | 29.4 | 38.7 | — | — | 1.48 |
| Coated Crystal | 6.8 | 13.3 | 23.4 | 34.5 | — | — | |
| Comp. Ex. F Tablet | 32.2 | 44.2 | 60.4 | 71.8 | — | — | 8.94 |
| Coated Crystal | 3.6 | 6.5 | 13.0 | 20.4 | 36.3 | 58.4 | |
| Comp. Ex. G Tablet | 27.6 | 43.3 | 61.7 | 74.6 | — | — | 9.52 |
| Coated Crystal | 2.0 | 5.0 | 10.3 | 16.5 | — | — | |
| Comp. Ex. H Tablet | 27.4 | 41.5 | 59.6 | 71.2 | — | — | 10.96 |
| Coated Crystal | — | — | — | 13.1 | 24.4 | 41.9 | |

See Table 2 for footnotes 6–7.

Figure 2A:
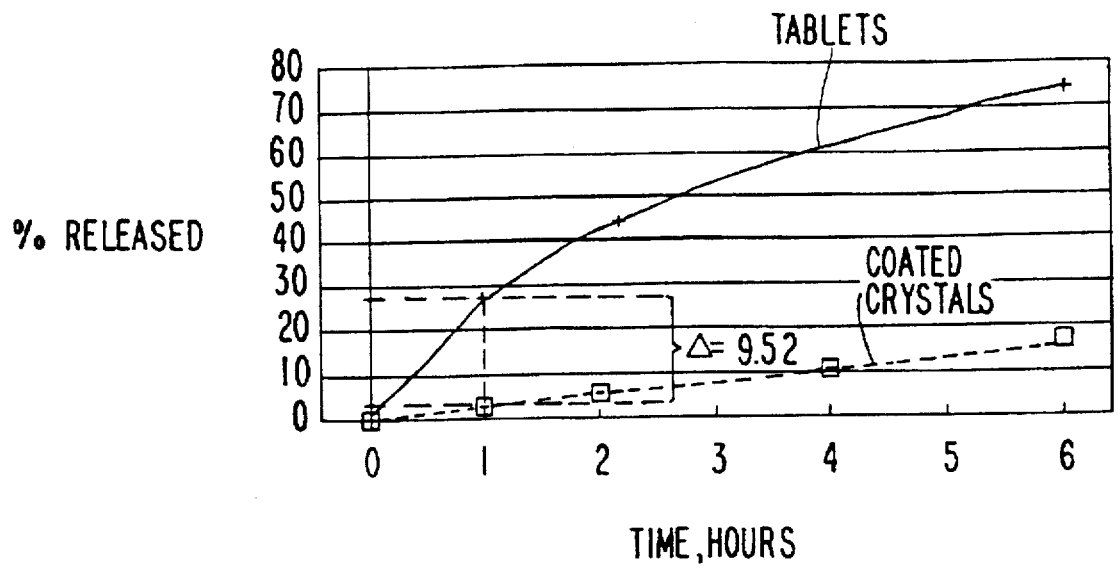
FIG. 2A, FIG. 2B and FIG. 2C are graphs showing the release characteristics of potassium bicarbonate crystals coated with an incompatible film-forming material and hydrophobic wax in accordance with Comparative Examples E–G, indicating the ratio Δ of the degree of dissolution of the salt in the entabletted dosage forms as compared with the degree of dissolution from the coated crystals prior to tabletting.
Figure 2B:
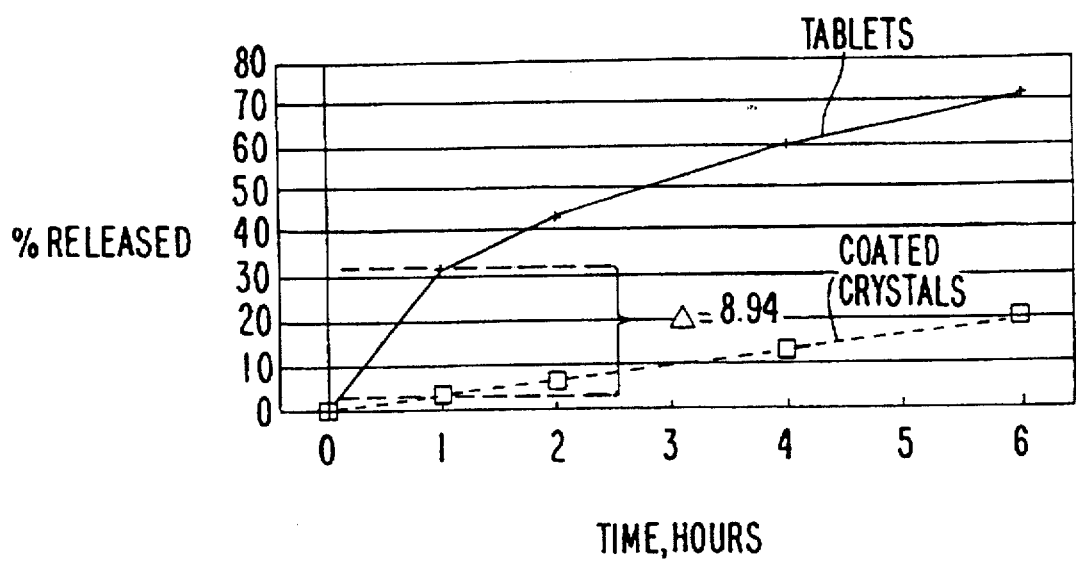
Figure 2C:
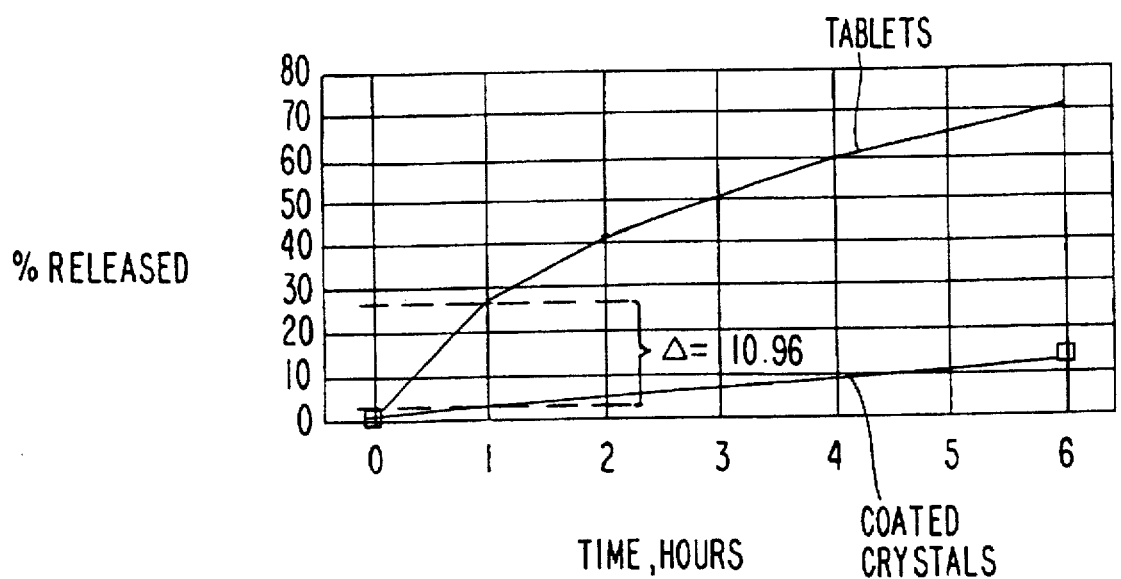

As shown in Table 7, and as is apparent from comparison of FIGS. 1A & B with FIGS. 2A, B & C, the ratio Δ of the % dissolution of tablets incorporating coated crystals comprising the incompatible film-former/wax mixtures to the % dissolution of the coated crystals prior to compaction into the tablet dosage form, demonstrates the reaction of such incompatible coating mixtures to compression during tabletting. The consequent inordinate increase of the release rates of the tabletted dosage forms prepared from such mixtures is in contrast to the ratios demonstrated by the dosage forms of the present invention diagrammed in FIGS. 1A & B. FIGS. 1A & B each demonstrate ratios A approaching one.

Further testing indicated that the damage to the crystal coatings demonstrated in FIGS. 2A, B & C was also reflected by stability problems upon storage of the tablets at slightly elevated temperatures and relatively high humidities (30°–40° C. and 70% RH).

While preferred embodiments of the invention have been described in the foregoing examples, it will be understood by those skilled in the art that various changes and modifications may be made therein without departing from the spirit and the scope of the invention. Accordingly, the above description should be construed as illustrative, and not in a limiting sense, the scope of the invention being defined by the following claims.

We claim:

1. A multiparticulate controlled release preparation incorporating an alkalinizing salt of potassium as an active ingredient and suitable for forming a pharmaceutical dosage form for oral administration, comprising:

(a) a multiplicity of single crystals of the alkalinizing potassium salt, the crystals having aspect ratios less than 3:1, particle sizes greater than 500μ, a weight mean particle size greater than 700μ, and a B.E.T. surface area less than 0.015 m$^2$/gram;

(b) a coating on each of the alkalinizing potassium salt crystals formed by deposition from a coating lacquer, comprising a hydrophobic wax and a compatible film-forming material selected from the group consisting of cellulose ethers and acrylic acid-based polymers, the hydrophobic wax and the film-forming material both being water-insoluble, being soluble in the same solvent, and being miscible with one another in the lacquer utilized to form the coating, and forming a strong yet thin, permeable membrane in the dried coating;

the coated crystals being capable of being tabletted in a dosage form wherein the alkalinizing potassium salt is at least 75% by weight of the tablet dosage form.

2. The multiparticulate controlled release preparation of claim 1, further comprising pharmaceutically acceptable excipients blended and compacted with the coated crystals to provide a tablet dosage form wherein the alkalinizing potassium salt is present in a dose density of at least 11.18 milliequivalents per c.c.

3. The tablet dosage form of claim 2, wherein the active ingredient comprises at least 75% by weight of the total tablet dosage form.

4. The tablet dosage form of claim 2, wherein the pharmaceutically acceptable excipient comprises:

(a) a binder in an amount of 1–10 weight % of the tablet dosage form;

(b) a hydrophobic wax which is the same as or is compatible with the hydrophobic wax in the crystal coating, present in an amount of 0.30–3.0 weight % of the unit dosage form; and (c) a disintegrant in an amount of 0–10 weight % of the tablet dosage form.

5. The tablet dosage form of claim 2, wherein each crystal coating is a single layer mixture of the hydrophobic wax in an amount of 0.25–3.0 weight % of the tablet dosage form, the film-forming material in an amount of 1–8 weight % of the tablet dosage form, and a plasticizer in an amount of 0–1 weight % of the tablet dosage form.

6. The tablet dosage form of claim 2, wherein each crystal coating comprises:

(a) a first, inner layer comprising the film-forming material, in an amount of 1–5 weight % of the tablet dosage form and a plasticizer in an amount of 0–1 weight % of the tablet dosage form, or the hydrophobic wax in an amount of 0.1–2.0 weight % of the tablet dosage form; and (b) a second, outer layer comprising the film-forming material, in an amount of 1–5 weight % of the tablet dosage form, the plasticizer in an amount of 0–1 weight % of the tablet dosage form, and the hydrophobic wax in an amount of 0.1–2.0 weight % of the tablet dosage form.

7. The tablet dosage form of claim 2, wherein each crystal coating comprises:

(a) a first, inner layer comprising the film-forming material, in an amount of 1–5 weight % of the tablet dosage form, a plasticizer in an amount of 0–1 weight % of the tablet dosage form;

(b) a second, intermediate layer comprising the hydrophobic wax, in an amount of 0.1–2 weight % of the tablet dosage form; and (c) a third, outer layer comprising the film-forming material, in an amount of 1–5 weight % of the tablet dosage form, the plasticizer in an amount of 0–1 weight % of the tablet dosage form, and the hydrophobic wax in an amount of 0.1–2.0 weight % of the tablet dosage form.

8. The controlled release preparation of claim 1, wherein the hydrophobic wax in the crystal coating is hydrogenated castor oil, and the film-forming material is ethylcellulose.

9. A multiparticulate controlled release preparation incorporating potassium bicarbonate as an active ingredient and suitable for forming a pharmaceutical dosage form for oral administration, comprising:

(a) a multiplicity of single crystals of the potassium bicarbonate, the crystals having aspect ratios less than 3:1, particle sizes greater than 500μ, a weight mean particle size greater than 700μ, and a B.E.T. surface area less than 0.015 m$^2$/gram;

(b) a coating on each of the potassium bicarbonate crystals formed by deposition from a coating lacquer, comprising a hydrophobic wax and a compatible film-forming material selected from the group consisting of cellulose ethers and acrylic acid-based polymers, the hydrophobic wax and the film-forming material both being water-insoluble, being soluble in the same solvent, and being miscible with one another in the lacquer utilized to form the coating, and forming a strong yet thin, permeable membrane in the dried coating;

the coated crystals being capable of being tabletted in a dosage form wherein the alkalinizing potassium salt is at least 75% by weight of the tablet dosage form.

10. The multiparticulate controlled release preparation of claim 9, further comprising pharmaceutically acceptable excipients blended and compacted with the coated crystals to provide a tablet dosage form wherein the potassium bicarbonate is present in a dose density of at least 11.18 milliequivalents per c.c.

11. The tablet dosage form of claim 10, wherein the potassium bicarbonate crystals have a weight mean particle size of 800–900μ, a specific B.E.T. surface area of 0.004–0.010 m$^2$/gram, particle distributions such that over 90 weight % of the crystals have particle sizes between 700 and 1000μ and a dose density of at least 13.0 milliequivalents per c.c.

* * * * *